United States Patent
Levy et al.

(10) Patent No.: US 6,740,519 B1
(45) Date of Patent: May 25, 2004

(54) IMMORTALIZED, HOMOZYGOUS STAT1-DEFICIENT MAMMALIAN CELL LINES AND THEIR USES

(75) Inventors: David Levy, New York, NY (US); Peter Palese, Leonia, NJ (US); Adolfo Garcia-Sastre, New York, NY (US); Joan Elizabeth Durbin, Columbus, OH (US)

(73) Assignees: Mount Sinai School of Medicine, New York, NY (US); New York University, New York, NY (US)

( * ) Notice: Subject to any disclaimer, the term of this patent is extended or adjusted under 35 U.S.C. 154(b) by 909 days.

(21) Appl. No.: 08/962,740

(22) Filed: Nov. 3, 1997

(51) Int. Cl.$^7$ ................................................. C12N 5/00
(52) U.S. Cl. .................... 435/325; 435/235.1; 435/352; 435/455
(58) Field of Search .................. 435/352, 455, 435/325, 235.1

(56) References Cited

U.S. PATENT DOCUMENTS

| | | | |
|---|---|---|---|
| 4,071,618 A | | 1/1978 | Konobe et al. |
| 5,087,571 A | * | 2/1992 | Leder et al. |
| 5,358,867 A | | 10/1994 | Revel et al. |
| 5,616,489 A | | 4/1997 | Levy |
| 5,648,217 A | | 7/1997 | Levy |
| 5,814,716 A | * | 9/1998 | Jallat et al. |

FOREIGN PATENT DOCUMENTS

WO          97/08292         3/1997

OTHER PUBLICATIONS

Horvath et al., "The Antiviral State Induced by Alpha Interferon and Gamma Interferon Requires Transcriptionally Active Stat1 Protein", *Journal of Virology*, vol. 70, No. 1, Jan. 1996, pp. 647–650.

Improta et al., "Susceptibility to virus infection in determined by a Stat–mediated response to the autocrine effect of virus–induced type I Interferon", *Cytokine*, vol. 9, No. 6, Jun. 1997, pp. 383–393.

Meraz et al., "Targeted Disruption of the Stat1 Gene in Mice Reveals Unexpected Physiologic specificity in the JAK–STAT signaling pathway", *Cell*, vol. 84, No. 3, Feb. 9, 1996, pp. 431–442.

Muller et al., "Complementation of a mutant cell line: central role of the 91 kDa polypeptide of ISGF3 in the interferon–α and 'Y signal transduction pathways", *EMBO Journal*, vol. 12, No. 11, 1993, pp. 4221–4228.

Durbin et al., "Influenza virus tropism is altered in teh absence of interferon signaling", *Journal of Interferon and Cytokine Research*, vol. 17, No. suppl 2, Oct. 1997, p. S48.

Garcia–Sastre, et al., "The Role of Interferon in Influenza Virus Tissue Tropism", *Journal of Virology*, vol. 72, No. 11, Nov. 1998, pp. 8550–8558.

Levy (1995) Semin Virol. 6:181–189.

Bluyssen et al. (1996) Cytokine Growth Factor Rev. 7:11–17.

Durbin et al. (1996) Cell 84:443–450.

Brown et al. (1997) Science 277:831–834.

Shindler et al. (1992) Proc Natl. Acad Sci. USA 89:7836–7839.

* cited by examiner

*Primary Examiner*—L Blaine Lankford
(74) *Attorney, Agent, or Firm*—Kenyon & Kenyon

(57) ABSTRACT

The present invention is directed to immortalized STAT1-deficient mammalian cell lines. STAT1 is a signal transducer and activator of transcription that becomes phosphorylated when cells are treated with type I or type II interferons and leads to induction of specific gene expression, resulting in establishment of the antiviral state and the other known biological responses to interferons, including the inhibition of cell proliferation. Cells which lack this gene product are useful for producing high titers of viral stocks, for producing recombinant viral vectors, for testing samples, especially clinical samples for the presence of virus and for screening candidate compounds or drugs for anti-viral activity.

1 Claim, No Drawings

IMMORTALIZED, HOMOZYGOUS STAT1-DEFICIENT MAMMALIAN CELL LINES AND THEIR USES

This invention was made in part with U.S. Government support under Grant No. AI28900 awarded by the National Institutes of Health. The Government has certain rights in the invention.

FIELD OF THE INVENTION

The present invention is directed to immortalized STAT1-deficient mammalian cell lines. STAT1 is a signal transducer and activator of transcription that becomes phosphorylated when cells are treated with type I or type II interferons and leads to induction of specific gene expression, resulting in establishment of the antiviral state and the other known biological responses to interferons, including the inhibition of cell proliferation. Cells which lack this gene product are useful for producing high titers of viral stocks, for producing recombinant viral vectors, for testing samples, especially clinical samples for the presence of virus and for screening candidate compounds or drugs for anti-viral activity.

BACKGROUND OF THE INVENTION

Interferon (IFN) treatment of cells leads to activation of a family of proteins termed signal transducers and activators of transcription, or STATs. The STAT proteins play a role in a cascade of events that leads to transcription of IFN stimulated genes (ISGs). The ISGs then mediate a multitude of well-known cellular responses to IFN such as induction of an antiviral state, inhibition of cellular proliferation, immune modulation, differentiation and resistance to bacterial and parasitic infections.

IFN induction of gene expression occurs through the Jak-STAT pathway. The molecular basis of this signal transduction and transcriptional activation pathway has been extensively studied and is reviewed by Levy (1995) Semin. Virol. 6:181–189 and Bluyssen et al. (1996) Cytokine Growth Factor Rev. 7:11–17.

STATs are constitutively-produced cytoplasmic proteins which are activated by tyrosine phosphorylation upon binding of IFN to its receptor. Cells treated with type I IFN(the family of proteins known as IFN α and IFN β) phosphorylate STAT1 and STAT2, whereas cells treated with type II IFN (or IFN γ) only phosphorylate STAT1. Evidence strongly suggests that phosphorylation is mediated by the Jak family of protein kinases which are associated with the IFN receptors and autophosphorylate when cells are treated with IFN.

Once activated, the STATs multimerize, translocate to the cell nucleus and form transcription factor complexes which bind to specific sequences of DNA in a manner dependent upon the type of IFN that stimulated the cells. In the absence of IFN stimulation, the STAT proteins do not exhibit complex formation, nuclear localization or DNA binding.

In addition to activation by the IFN system, STAT1 is also activated by a variety of cytokines and growth factors, including IL-6, leukemia inhibitory factor (LIF), oncostatin M, growth hormone, IL-10, epidermal growth factor (EGF), platelet-derived growth factor (PDGF), colony-stimulating factor 1 (CSF-1) and angiotensin II [Durbin et al. (1996) Cell 84: 443–450].

Recently, STAT1 knockout mice were prepared (Durbin, 1996). STAT1 knock out mice are homozygous for a null allele of the murine Stat1 gene, i.e., Stat1$^{-/-}$, and produced by targeted disruption of the Stat1 gene. The cDNA sequence of the murine Stat1 gene is available as GenBank accession number U06924. The disrupted Stat1 gene was cloned into tranfection vector pPNT. That linearized construct was transfected into murine embryonic stem cells (ES cells) and cultured in the presence of G148 and gancyclovir. Homozygous ES cell lines were isolated by culturing with high concentrations of G148.

The Stat1$^{-/-}$ animals were obtained by injection of heterozygous Stat1$^{+/-}$ ES cells into normal mouse blastocysts and interbreeding to produce the homozygous progeny. The STAT1 knockout mice were born at normal frequency, had no gross developmental defects (as might be expected if the cytokine or growth factor signaling pathways sensitive to STAT1 had been disrupted) but were highly susceptible to viral diseases, including mouse hepatitis virus (MHV), vesicular stomatitis virus (VSV) and influenza virus. There was no transcriptional response to IFN in isolated tissues (splenocytes and macrophages) of STAT1 knockout mice. However, when the macrophages were treated with IL-6, a cytokine, the transcriptional response was normal.

SUMMARY OF THE INVENTION

This invention is directed to immortalized Stat1$^{+/+}$ mammalian cell lines preferably of murine or human origin. Such cell lines can be obtained from STAT1 knockout animals or can be prepared by converting cultured cells to homozygosity for a Stat1 null allele, followed by immortalization if necessary. Immortalized cell lines can be obtained spontaneously or by transformation with a transforming agent such as SV40 T antigen or other oncogene.

The cell lines of the invention are preferably endothelial cells, epithelial cells, hematopoetic cells, bone marrow cells, kidney cells or liver cells. Most preferably the cell lines are murine or human fibroblasts and bone marrow cells.

Another aspect of the invention relates to a method of producing a viral stock by (a) infecting immortalized Stat1$^{-/-}$ mammalian cells of the invention with a virus, (b) culturing the infected cells under conditions and for a time sufficient to allow replication of that virus and (c) recovering the so-produced virus to obtain the viral stock. The cells can be either adherent cells or non-adherent cells. Infections are typically done at a multiplicity of infection (MOI) of about one or less and can result in viral titers ranging from about $10^2$ plaque forming units per milliliter (PFU/mL) to more than $10^6$ (PFU/mL) depending on the virus, the MOI and growth conditions.

The cell lines of the invention are particularly useful for producing viral stocks from a wide variety of viruses, including viruses not typically grown in that cell type since the STAT1-deficient cell lines show altered viral tropism. Hence, viral stocks can be prepared, for example, for influenza virus, parainfluenza virus, measles virus, respiratory syncytial virus (RSV), hepatitis viruses, adenovirus, herpes viruses or vesicular stomatitis virus.

Yet another aspect of this invention is directed to a method of producing a recombinant viral vector by (a) infecting or transfecting immortalized Stat1$^{-/-}$ mammalian cells with the recombinant viral vector, (b) culturing those cells under conditions and for a time suffcient to allow replication of that vector, and (c) recovering the vector. The method is applicable to recombinant viral DNA and RNA vectors, and is particularly useful for vectors such as adenovirus vectors, retrovirus vectors or sindbis virus vectors. Vectors which can be used in gene therapy can also be prepared by this method.

Still further the present invention provides a sensitive method for detecting the presence, absence or quantity of a virus in a sample by (a) contacting immortalized Stat1$^{-/-}$ mammalian cells with a test sample, (b) culturing those cells under conditions and for a time to allow replication of any virus that may be present in the test sample, and (c) recovering, if necessary, and identifying and/or quantitating the virus. The test sample is typically a clinical sample and can be treated to remove particulates or a viral extract can be prepared therefrom and used as the testing sample. Clinical samples include but are not limited to body fluids, body tissues or other bodily materials. The identity of the virus can be determined by immunoassay, polymerase chain reaction or nucleic acid hybridization using a viral-specific reagent. When desired, quantitation of the virus can be accomplished by serial dilution of the test sample and culturing as above to determine the end point of viral infection.

Yet still another aspect of the invention is directed to providing a method for screening compounds for antiviral activity. Immortalized Stat1$^{-/-}$ mammalian cells are treated with a candidate compound and infected with a virus against which antiviral activity is sought. The cells can be exposed to the compound for various periods of time prior to, concurrently, or after viral infection. The cells are cultured for a time and under conditions to allow replication of the infecting virus and the amount of viral production in treated cells is determined relative to viral production in an untreated control cell line. The decrease in virus production provides a means to measure the antiviral activity of the test compound and can be determined qualitatively or quantitatively. For example, viral production can be determined by assessing the change in cytopathic effect or plaque formation of the virus on indicator cells. Similarly, the amount of virus can be determined by immunoassay, by polymerase chain reaction (PCR) or by nucleic acid hybridization using a virus-specific reagent. Compounds can be tested for antiviral activity against individual viruses, families of viruses or combinations of several viruses. Antiviral activity of the compounds can be determined for any virus capable of replication in a Stat1$^{-/-}$ cell line, including, but not limited to, influenza virus, parainfluenza virus, measles virus, RSV, hepatitis viruses, adenovirus, herpes viruses, vesicular stomatitis virus, retroviruses including human immunodeficiency virus (HIV) and sindbis virus.

DETAILED DESCRIPTION OF THE INVENTION

The general techniques used for the subject invention, including constructing the vectors used in targeting cells, creating knockout animal strains, performing deletion analysis and RFLP analysis, transforming cells, growing cells in culture, and the like are known in the art and laboratory manuals are available describing these techniques.

Unless otherwise indicated, the present invention employs known techniques of molecular biology, cell culture and recombinant DNA which are within the skill of the art. Examples of useful laboratory manuals include Sambrook et al. (1989) Molecular Cloning: *A Laboratory Manual*, 2nd Ed., Cold Spring Harbor Laboratory Press, Cold Spring Harbor, N.Y.; Miller et al. (1987) Gene Transfer Vectors for Mammalian Cells, Cold Spring Harbor Laboratory Press, Cold Spring Harbor, N.Y.; Hogan et al. (1994) *Manipulating the Mouse Embryo*, A Laboratory Manual. Cold Spring Harbor Laboratory Press, Cold Spring Harbor, N.Y.; Jakoby & Pastan (1979) Meth. Enzymol. 58, *Cell Culture*; and Joyner (1993) *Gene Targeting*, A Practical Approach, Oxford University Press, Oxford.

STAT1 knockout mice are homozygous for a null allele of the Stat1 gene and are unable to respond to type I or II IFN. While these animals appear normal at birth, they are highly susceptible to viral infection and succumb to viral diseases that are either non-lethal in wild type animals or at much lower doses than do wild type animals. It has now been discovered that immortalized or transformed cells from STAT1 knockout mice can be obtained which produce unexpectedly high titers of virus and exhibit altered viral tropism. These cells are particularly useful for preparing viral stocks that can be used for a variety of purposes, including vaccine preparation. The cells of the invention are useful for preparing viral stocks of viruses with limited host range specificity or with undesirable host range specificity. For example, influenza virus is prepared in eggs for the yearly-changing flu vaccine. The demand for flu vaccine is high and production needs often can not be satisfied through this propagation technique. Moreover, persons allergic to eggs can not receive these flu vaccines since viruses propagated in eggs have residual egg antigens that cause allergic reactions. The altered host range specificity also makes the STAT1-deficient cells an excellent host for preparing recombinant viral vectors, particularly for vectors with gene therapy applications.

Since STAT1-deficient cell lines produce high titers of virus, these cells provide a sensitive means to detect, diagnose and quantitate the presence of virus in clinical samples or other samples, especially samples containing a low number of infectious units. For example, a clinical sample obtained from a patient suspected of having a particular viral pathogen or with symptoms characteristic of one or more viral pathogens can be cultured with a STAT1-deficient cell line. After a period to allow for viral replication, the cultured cells are examined by any of numerous techniques for the presence or absence of the suspected pathogen(s) using viral-specific detection reagents or means.

Moreover, because STAT1-deficient cells are sensitive indicators for viral production, these cells are also useful for screening candidate compounds for antiviral activity. For example, cells of the invention are co-cultured with a candidate compound and specific virus to determine the effect on viremia, e.g., whether virion production is decreased, or whether cytopathic characteristics of that virus can be altered.

Accordingly, the present invention is directed to immortalized $Stat1^{-/-}$ mammalian cell lines. As used herein, "immortalized" and "transformed" are used interchangeably to mean a cell line which is no longer a primary cell line, but which has been adapted to grow indefinitely in tissue culture. Such cell lines can be obtained by selecting for cells which become spontaneously immortalized or which have been transformed with a transforming agent that enables the cell to grow permanently in culture. The immortalized cell lines of the invention include adherent cells, i.e., cells which are grown by attaching to a surface or substrate capable of supporting cell growth, or non-adherent cells, e.g., cells which can be grown in a liquid spinner culture.

As used herein, a Stat1 null allele represents a Stat1 gene that produces either no detectable STAT1 protein or a non-functional STAT1 protein.

As used herein "mammalian cell lines" and "mammalian cells" include cell lines or cells from any mammal such as from humans, lab animals, domesticated animals and others. The preferred cells lines are from mice, humans, rats, cows, dogs, cats, pigs, sheep or other animals, and more preferably from mice or humans.

The cell lines of the invention are directed to cells that are immortalized and can be maintained indefinitely in culture.

These cells are preferably endothelial cells, epithelial cells, hematopoetic cells, bone marrow cells, kidney cells or liver cells. Epithelial cells include all types of fibroblasts, especially mouse embryonic fibroblasts. The hematopoetic cells of the invention include macrophages, B cells, T cells or monocytes or any other hematopoetic cell line which can be immortalized and grown in tissue culture. Bone marrow cells represent a mixture of cell types and include pluripotent stem cells, fibroblasts, osteoblasts and others. As above, any bone marrow cell which can be immortalized and grown in tissue culture is contemplated by the invention. More preferably the cell lines are fibroblasts, macrophages and bone marrow cells, and most preferably, murine fibroblasts. The cell lines of the invention do not include naturally immortal cells, e.g., embryonic stem cells, which are cells that grow indefinitely in culture without being treated to cause immortalization.

A representative cell line of the invention has been deposited with the American Type Culture Collection 1; (ATCC) 12301 Parklawn Drive, Rockville, Md. 20852 USA in accordance with the requirements of the Budapest Treaty on Oct. 31, 1997. This cell line is mouse embryo fibroblast cell line CD1-Stat1$^{-/-}$ Isa and assigned accession ATCC number CRL-12425

The cell lines of the invention are obtained from STAT1 knockout animals or are prepared by converting cultured cells of an appropriate cell line to STAT1 deficiency, i.e., by creating homozygous Stat1 null alleles in the cell line and immortalizing it if necessary.

Some mammals can be genetically manipulated in vitro, e.g., via embryonic stem cells or other methods, to create mutations that are used for embryo implantation to produce heterozygous animals. These heterozygotes can then be crossbred to yield homozygous Stat1-deficient animals as generally described by Durbin (1996). This method is particularly applicable to mice. For those mammals which can not be genetically manipulated in vitro, such as humane, Stat1 null alleles can be introduced into a cultured cell line using the vectors, targeting method of ES cells, and modes of analysis as generally described by Durbin (1996) in combination with a second targeting event as generally described by Brown et al. (1997) Science 277:831. Those of ordinary skill in the art recognize that the targeting can be accomplished with any suitable targeting vectors and by selecting for cells which have taken up the vector by any number of means, including antibiotic resistance, or other marker gene. Marker genes can be assayed by conventional means known in the art including enzymatic activity, histochemical localization, immunoassay, calorimetric assay, and fluorescence.

When targeting a Stat1 gene, it is preferable but not necessary if sufficient homology exists between the gene pair being used, that the Stat1 gene of the targeting vector be the same as that in the targeted species. This preferred species matching applies to preparation of STAT1-deficient animals or STAT1-deficient cultured cells. The mouse Stat1 gene DNA is available from GenBank under accession number U06924 and the sequence of exons of the corresponding human gene under accession numbers U18662-U18670. The human Stat1 gene is described by Schindler et al. (1992) Proc. Natl. Acad. Sci. USA 89:7836-7839.

Cell lines established from STAT1 knockout animals are immortalized for indefinite growth in tissue culture. STAT1-deficient cell lines established from cultured cells are subjected to an immortalization step if those cells are not already immortalized. If this immortalization step is necessary, it can be conducted prior to or after the cells are made homozygous for a Stat1 null allele.

Immortalized cell lines can be obtained spontaneously by repeatedly subculturing cells until indefinitely, e.g., permanently, growing cells are established. Once established, such cells can be diluted and clonally propagated by standard techniques to yield a cell line arising from a single immortalized cell. Cell lines of the invention which can be spontaneously immortalized include murine and human cell lines. One method for selection of spontaneously immortalized cells is provided by Todaro et al. (1963) J. Cell. Biol. 11:299-313.

Immortalized cells can also be obtained by transformation with a transforming agent such as the SV40 virus, the SV40 T antigen, another transforming virus or an oncogene using techniques known in the art. In addition to the foregoing, other known transformation agents include polyoma virus oncogenes and Src oncogenes. Murine B lymphocytes can be transformed by Abelson murine leukemia virus. As an example, wild type or temperature sensitive SV40 virus (SV40ts) can be used to transform cells according to the method of Chou (1985) Meth. Enzym. 109:385–396. Cell types which can be readily transformed by this method include epithelial cells, endothelial cells, bone marrow cells and others.

Transformation can be accomplished by any method which allows uptake and stable establishment of the virus or transforming agent in the cell line such as, for example, direct uptake of a vector by calcium-phosphate precipitation, lipid-mediated transfection, transfection, transduction, or electroporation. The transforming agent or virus may be maintained as a non-integrated vector, for example, a plasmid, or alternatively, may be integrated into the host genome so long as it can be stably maintained. Transformation methods are provided, for example, by Sambrook et al.

Another aspect of the invention provides a method of producing a viral stock by (a) infecting immortalized Stat1$^{-/-}$ mammalian cells of the invention with a virus, (b) culturing the infected cells under conditions and for a time sufficient to allow replication of that virus and (c) recovering the so-produced virus to obtain the viral stock.

The immortalized Stat1$^{-/-}$ mammalian cells for this method are as described hereinabove.

The STAT1-deficient cell lines show altered viral tropism, making this method of producing viral stocks applicable for propagation of a wide variety of viruses. Hence, viruses can be grown in STAT1-deficient cells that would not otherwise be permissive for such growth, e.g., influenza virus is incapable of propagation in wild type fibroblast whereas it is capable of high titer growth in STAT1-deficient fibroblasts. Accordingly, viral stocks that can be prepared in the immortalized STAT1-deficient cells of the invention include, but are not limited to, influenza virus, parainfluenza virus, measles virus, respiratory syncytia virus (RSV), hepatitis viruses, adenovirus, herpes viruses or vesicular stomatitis virus. The hepatitis viruses include hepatitis A, hepatitis B and hepatitis C virus. Herpes viruses include cytomegalovirus, herpes simplex virus I and II, chickenpox virus, mumps virus, herpes virus VIII (Kaposi's sarcoma virus) and Epstein-Barr virus.

Since these viral stocks are useful for preparing vaccines, viral stocks can also be prepared for attenuated or non-virulent forms of these viruses or any other viral form that would be suitable for use in a vaccine and which is propagated in cell culture.

In accordance with the invention either adherent cells or non-adherent cells can be infected with virus. Methods of infecting cells with virus are well known in the art. The choice of which type of cells to use depends on the cellular growth properties, the virus and the infection conditions. When infecting adherent cells, infectious virus is added to the cells at a time selected to maximize virion production. That time can be determined by the nature of the virus, and any known cellular stage for infection or time of infection. For example with influenza virus, infections are preferably done when the cells are nearly confluent or are at confluency since this tends to maximize the number of infected cells and thereby provide a greater burst size of virions.

The MOI depends on the nature of the virus, the cell line being used for infection, the infection conditions and the time of infection. MOI is defined as the number of virus particles or infectious units per cell. Typically an MOI of about one or less is used, but can range to as low as about 0.001 or as high as about 1000 depending on the virus. For influenza virus the MOI on the fibroblast cells of this invention ranges from about 0.001 to about 1.

After infection, the cells are cultured for a time and under conditions to allow replication and production of the virus. Cells are incubated as long as necessary to achieve maximal virus production. Typically, titers can be achieved ranging from about $10^2$ plaque forming units per milliliter (PFU/mL) to more than $10^6$ (PFU/mL) depending on the virus, the MOI and growth conditions. For influenza virus, titers of $10^3$ to $10^6$ can be obtained in 2 to 3 days. VSV can produce titers of greater than $10^7$.

Once productive infection is at a maximum, virus can be harvested, isolated and purified as needed. Virus can be harvested from the supernatent or from the cells depending on the nature of viral production. The techniques for viral harvesting, isolation and purification depend on the nature of virus production (i.e., release into the supernatent or accumulation within the cell), the properties of the virus and are generally known in the art or can be readily determined.

In another embodiment, the instant invention provides a method of producing a recombinant viral vector by (a) infecting or transfecting immortalized Stat1 mammalian cells with the recombinant viral vector, (b) culturing those cells under conditions and for a time sufficient to allow replication of that vector, and (c) recovering the vector.

As used herein, a "recombinant viral vector" means a recombinantly-manipulated viral vector which has been engineered so as to be capable of expressing one or more heterologous or foreign genes and can be used as a transfer vector to introduce those gene(s) into a host cell. The viral vector is composed of at least a nucleic acid moiety, either DNA or RNA, and can be a plasmid, linear nucleic acid or virion nucleic acid. The viral vector can be encapsidated as a virus, bound in a complex with protein and/or other nucleic acids or can consist of nucleic acid alone. While the viral vector must be capable of replication and hence duplication in the STAT1-deficient cell lines, it need not be capable of replicating and producing infectious virions in other hosts. Typically, the viral vector is a gene therapy vector and includes recombinant viral DNA and RNA vectors, especially recombinant viral vectors such as adenovirus vectors, retrovirus vectors or sindbis virus vectors.

The conditions and requirements for preparing recombinant viral vectors in the STAT1-deficient cells of the invention are similar to those employed for preparing viral stocks.

A still further embodiment of the invention relates to a sensitive method for detecting the presence or absence of a virus in a sample by (a) contacting immortalized Stat1$^{-/-}$ mammalian cells with a test sample, (b) culturing those cells under conditions and for a time to allow replication of any virus that may be present in the test sample, and (c) recovering and identifying the virus. Once the suspected virus is detected and identified, then that information can be used in diagnosis of viral conditions and diseases as well as in planning appropriate therapeutic regimens. Moreover, lack of detection of suspected viral pathogens, can provide at least some aid in ruling out particular conditions. In addition, this method can be adapted for quantitation of the amount of virus in a clinical sample, e.g., by serial dilution of the test sample and determination of that titer of virus which no longer yields productive infection (or by determining some other appropriate indicator for the presence of infectious virus).

The immortalized Stat1$^{-/-}$ mammalian cells used in this method are as described hereinabove. The viruses which can be detected in test samples include those previously described herein and any others capable of growing in a STAT1-deficient cell line. Culturing conditions are also as described hereinbefore.

The test sample is typically a clinical sample obtained from a bodily fluid, body tissue or any other bodily material suspected of containing the virus. Body fluids which can be screened include blood and blood fractions (e.g. plasma and serum), saliva, urine or any other fluid which is suspected of containing a virus. The test sample, and especially clinical test samples can be treated to remove particulate material if necessary. Also an extract can be prepared from a sample and that extract applied to the cell line of the invention for testing. Extracts can be prepared by known techniques. One method to prepare an extract is to treat a sample with a solution, preferably a buffered solution compatible with the suspected virus(es), for a time and under conditions wherein the virus is removed from the sample and becomes solubilized or suspended in the solution.

The identity of the virus can be determined by immunoassay, polymerase chain reaction or nucleic acid hybridization using a viral-specific reagent.

To detect virus by immunoassay in accordance with the present invention, any immunoassay technique can be used with a viral-specific reagent. As used in an immunoassay, a viral-specific reagent is an antibody (monospecific polyclonal or monoclonal) or antiserum that binds specifically to and is a marker for recognition of the virus being detected. In the case of sandwich assays, the viral-specific reagent can represent two or more antibodies, antisera or any combination thereof that retains specificity for the virus being detected. Sandwich assays can also be used wherein one of the viral-specific reagents is a viral antigen. Examples of immunoassays useful to identify the viruses in accordance with the invention include, but are not limited to, an enzyme-linked immunoadsorbent assay (ELISA), an enzyme immunodot assay, a passive hemagglutination assay (e.g., PHA test), an antibody-virus-antibody sandwich assay, a virus-antibody-virus(or viral antigen) sandwich assay, or other well-known immunoassays including immunofluorescence. In accordance with the present invention, any suitable immunoassay can be used with the subject peptides. Such techniques are well known to the ordinarily skilled artisan and have been described in many standard immunology manuals and texts, see for example, by Harlow et al. (1988) Antibodies: *A Laboratory Manual*, Cold Spring Harbor Laboratory Press, Cold Spring Harbor, N.Y., 726 pp.

To detect virus by PCR, virus is recovered and the nucleic acid therein is amplified for PCR using viral-specific oligonucleotides as the viral-specific reagent. If necessary, RNA is first reverse-transcribed into DNA using reverse transcriptase in conjunction with either specific or random primers. If sufficient nucleic acid is available after amplification, then the amplified nucleic acid can be visualized directly on a gel and the virus thereby identified. To detect virus by nucleic acid hybridization, the virus is recovered and the nucleic acid thereof is isolated for analysis by nucleic acid hybridization using a virus-specific hybridization probe as the viral-specific reagent. These techniques are well known in the art and variations or combinations thereof can be used to identify virus.

Yet another aspect of the invention provides a method for screening compounds for antiviral activity. Immortalized Stat1$^{-/-}$ mammalian cells are treated with a candidate compound and infected with a virus against which antiviral activity is sought.

The immortalized Stat1$^{-/-}$ mammalian cells used in this method are as described hereinabove. The viruses which can be detected in test samples include those previously described herein and any others capable of growing in a STAT1-deficient cell line. Culturing conditions are also as generally described hereinbefore unless noted otherwise.

In accordance with this method, the cells of the invention are treated with the candidate compound for various periods of time prior to, concurrently, or after viral infection. The time periods before or after viral infection can also be varied when testing a compound for anti-viral activity.

Once treated, the cells are cultured for a time and under conditions to allow replication of the infecting virus. Untreated control cells, i.e., STAT1-deficient cells which have not been exposed to the candidate compound, are prepared and handled in a manner identical to the treated cells. The amount of viral production in the treated cells can then be determined relative to viral production in the untreated control cell line.

As used herein, "anti-viral activity" means the ability of a compound to effect a decrease in virus production, to effect a beneficial change in viral cytopathicity in vitro, or to otherwise reduce or ameliorate the effects of the virus on the cells of the invention. Such changes in in vitro characteristics of viral pathogenesis are indicative that the compound has in vivo therapeutic activity against the virus under study.

The antiviral activity of the test compound can be determined qualitatively or quantitatively. For example, viral production can be determined by assessing the change in cytopathic effect on indicator cells or plaque formation of the virus on indicator cells. Similarly, the amount of virus can be determined by immunoassay, by polymerase chain reaction (PCR) or by nucleic acid hybridization using a virus-specific reagent as described above.

Compounds can be tested for antiviral activity against individual viruses, families of viruses or combinations of several viruses. Antiviral activity of the compounds can be determined for any virus capable of replication in a $Stat1^{-/-}$ cell line, including, but not limited to, influenza virus, parainfluenza virus, measles virus, RSV, hepatitis viruses, adenovirus, herpes viruses, vesicular stomatitis virus, retroviruses including human immunodeficiency virus (HIV) and sindbis virus.

It is to be understood and expected that variations in the principles of invention herein disclosed in an exemplary embodiment may be made by one skilled in the art and it is intended that such modifications, changes, and substitutions are to be included within the scope of the present invention.

EXAMPLE 1

Preparation of Immortalized $Stat1^{-/-}$ A Murine Cell Lines

Embryos are obtained from $Stat1^{-/-}$ mice grown according to Durbin (1996) using the following strains: CD1-$Stat1^{-/-}$, (129xB6)F1-$Stat1^{-/-}$, C57BL6-$Stat1^{-/-}$ and 129-$Stat1^{-/-}$ . Primary cultures of mouse embryo fibroblasts (MEF) are prepared from 14 to 16 day embryos as described in Hogan et al. (1994) pp. 260–261. Cell lines are prepared from single embryos.

Immortalized cell lines are obtained by the method of Todaro (1963) by plating $5\times10^5$ mouse embryo fibroblast cells in a 60 mm culture dish in DMEM with 10% fetal calf serum and growing those in a 5% $CO_2$ atmosphere at 37° C. The cells are replated and grown under the same conditions every 3 days. Cells are considered established and immortalized when cellular growth is robust and doubling time is about 24 to 30 h. At least three independent cell lines are established for each strain. The immortalized cell lines are frozen in liquid nitrogen and stored.

The immortalized cell lines are tested for replication of human influenza viruses A/WSN/33 and PR8 by infecting confluent cells at an MOI of 0.001 with the influenza virus in PBS containing 0.2% BSA for 1 h at room temperature. After removing the virus inoculum, DMEM containing 0.2% BSA is added, and the cells are incubated at 37° C. for 2~3 days. Supernatents are then collected and assayed for virus production. The $Stat1^{-/-}$ cell lines prepared as above demonstrated titers of influenza virus ranging $10^4$ to $10^7$ PFU/ml whereas immortalized $Stat1^{-/-}$ cell lines prepared as described above and tested in an identical manner did not support production of human influenza virus.

EXAMPLE 2

Preparation of Transformed $Stat1^{-/-}$ Murine Cell Lines

Cultured murine bone marrow cells from a $Stat1^{-/-}$ mouse are infected with SV40-tsA virus at an MOI of 5–20 PFU per cell according to the method of Chou (1985). Briefly, after 2–3 h of virus adsorption at 33° C., the virus-containing solution is removed and the cells are incubated in low serum medium (4–5t) for 24 h. The cells are treated with trypsin and subcultured at low density to obtain individual clones with growth medium being changed every 3–4 days until visible clones are present, approximately two weeks post-infection. Individual clones are then isolated and propagated.

EXAMPLE 3

Preparation of Immortalized $Stat1^{-/-}$ Human Cell Lines

Normal human diploid fibroblasts are made heterozygous for a STAT1 deficiency (i.e., $Stat1^{-/-}$) by targeted disruption of the Stat1 gene according to the strategy and constructs used with the mouse ES cells as described in Durbin 1996 except the human Stat1 gene is used. The disrupted Stat1 gene is cloned into tranfection vector PPNT, which is then linearized, transfected into the fibroblasts and cultured in the presence of G418 and gancyclovir. Homozygous STAT1 deficienct fibroblast cell lines (i.e., $Stat1^{-/-}$ cells) are isolated by a second targeting event according to the method of Brown et al. (1997) Science 277:831, except that the neomycin-resistance cassette of the transfection vector is replaced with a hygromycin-resistance cassette and the cells are cultured in the presence of hygromycin and gancyclovir. The cells lines can be tested for heterozygosity and homozygosity by RFLP analysis.

After selection and establishment of a $Stat1^{-/-}$ human cell line, immortalized cells can be obtained as described in Example 2 by transformation with SV40 T antigen or by another transforming agent such as an oncogene.

EXAMPLE 4

Influenza Virus Susceptability of Immortalized $Stat^{1-/-}$ Murine Cell Lines

Immortalized MEF from wild type and STAT1-deficient mice are grown to confluency in 35 mm dishes (approximately $10^6$ cells) and incubated with $10^3$ pfu per dish of influenza A/WSN/33 in PBS containing 0.2% BSA for 1 h at room temperature. After removing the virus inoculum, 2 mL of DMEM containing 0.2% BSA is added and the cells are incubated at 37° C. Every 12 h a small volume of the medium is harvested and assayed for hemagglutination in (HA) activity with chicken red blood cells and for plaque forming ability on Madin-Darby canine kidney (MDCK) cells as generally described by Schulman et al. (1977) J. Virol. 24:170–176. These HA results are shown in Table 1 and the plaque assay results are shown in Table 2. In another experiment, immortalized MEF from wild type and STAT1-deficient mice are treated as above except that the MOI is varied from 0.001 to 1. These HA titer results are shown in Table 3.

TABLE 1

| Hemagglutinin Titers | | |
|---|---|---|
| Time P.I.[a] (h) | Stat1 +/+ | Stat1 −/− |
| 12 | n.d.[a] | n.d. |
| 24 | n.d. | n.d. |
| 36 | n.d. | n.d. |
| 48 | n.d. | 16 |
| 60 | n.d. | 32 |
| 72 | n.d. | 64 |

[a]Abbreviations for all tables: P.I., post infection; n.d., not detected.

TABLE 2

| Plaque Assays | | |
|---|---|---|
| Time P.I. (h) | Stat +/+ (PFU/mL) | Stat −/− (PFU/mL) |
| 12 | <10 | 30 |
| 24 | <10 | $5 \times 10^3$ |
| 36 | <10 | $4 \times 10^4$ |
| 48 | <10 | $5 \times 10^6$ |
| 60 | <10 | $6 \times 10^6$ |
| 72 | <10 | $3 \times 10^6$ |

TABLE 3

| Hemagglutinin Titer | | |
|---|---|---|
| MOI | Stat +/+ | Stat −/− |
| 0.001 | n.d. | 16 |
| 0.01 | n.d. | 64 |
| 0.1 | n.d. | 256 |
| 1.0 | n.d. | 256 |

We claim:

1. An immortalized mammalian cell line homozygous for a Stat1 null allele, wherein viral tropism of said cell line has been altered to be permissive for viral growth relative to that of the same cell line with wild type alleles of Stat1, and; wherein the cells of said cell line are fibroblast cells capable of producing influenza virus at from about $10^3$ to about $10^6$ PFU/ml at about two days after having been infected.

* * * * *